United States Patent
DuBois

[19]

[11] Patent Number: 6,094,999
[45] Date of Patent: Aug. 1, 2000

[54] ROTATABLE BATCH SAMPLER WITH WEDGE-SHAPED CONE

[76] Inventor: Delevan Andrew DuBois, 12 Thornton La., Piscataway, N.J. 08854

[21] Appl. No.: 09/224,461

[22] Filed: Dec. 31, 1998

[51] Int. Cl.$^7$ .................................................. G01N 1/16
[52] U.S. Cl. ...................................... 73/864.64; 73/863.31
[58] Field of Search ........................... 73/864.64, 863.31; 175/20, 58

[56] References Cited

U.S. PATENT DOCUMENTS

| | | | |
|---|---|---|---|
| 3,218,869 | 11/1965 | Fields et al. | 73/864.64 |
| 4,072,059 | 2/1978 | Hamilton | 73/864.64 |
| 4,800,765 | 1/1989 | Nelson | 73/864.64 |
| 5,377,551 | 1/1995 | Vacquer | 73/864.64 |

*Primary Examiner*—Robert Raevis
*Attorney, Agent, or Firm*—Ezra Sutton

[57] ABSTRACT

A rotatable sampling device for obtaining at least one sample of a dry powder blended material from the powder blend matrix within a container. The sampling device includes a sample collection member, an insert rod member and a sampler extension member. The sample collection member includes a substantially tubular housing having a front section, a middle section and a rear section. The front section includes a tapered wedge-shaped cone tip for inserting into the blend matrix to be sampled. The middle section includes a center wedge-shaped section for use in the collection of at least one sample of the blend matrix; and the center wedge-shaped section further includes at least one interior insert chamber for receiving in each a sample collection cup for collecting a sample of the blend matrix. The rear section includes a tapered wedge-shaped cone section for preventing the sampling device from moving relative to the Z axis as the sampling device is inserted within the blend matrix. The sample collection member also includes the insert rod member for rotating at least one sample collection cup within at least one interior insert chamber.

54 Claims, 11 Drawing Sheets

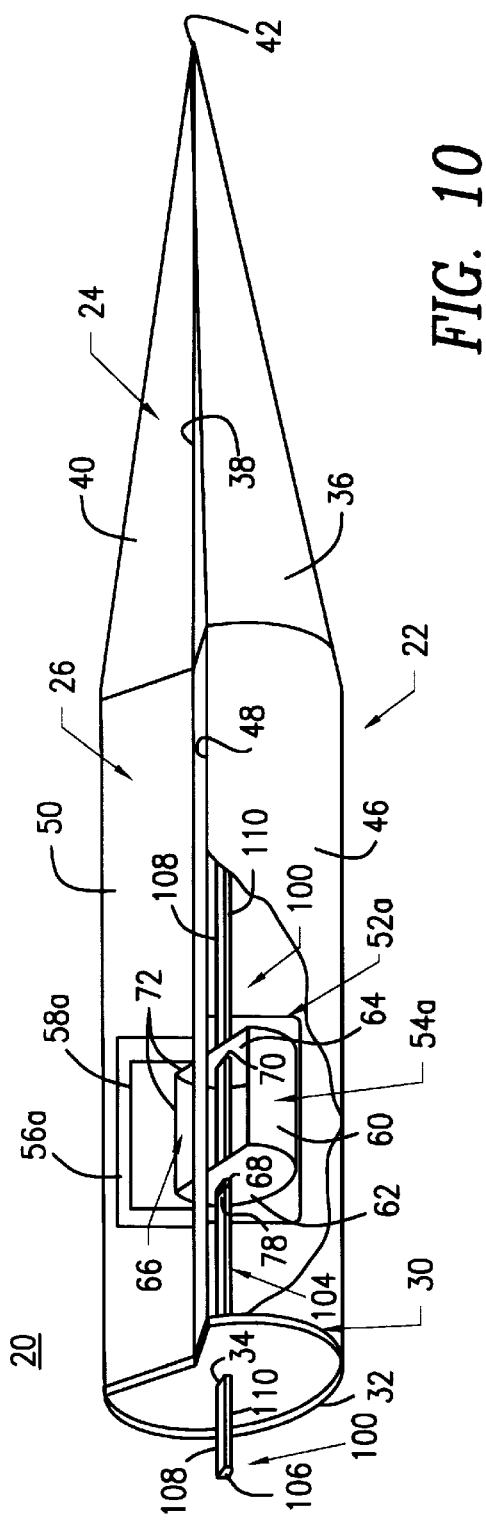

ROTATABLE BATCH SAMPLER WITH WEDGE-SHAPED CONE

FIELD OF THE INVENTION

The present invention relates to a sampling device and a method for using this sampling device. More particularly, this sampling device includes a wedge-shaped cone tip in order to facilitate the taking of a plurality of precise samples of dry powder blends at various depths simultaneously by utilizing sampling cups. This sampling device enables the procurement of these dry powder blend samples without appreciably disturbing the powder blend matrix or the composition of the matrix in order to obtain accurate quality control samples from very large blenders, mixers, tote bins, drums or fiber containers.

BACKGROUND OF THE INVENTION

In the manufacture of solid dosage forms (tablets, caplets, or pills) of pharmaceutical solids and semi-solid dosage forms (gel-tabs) of pharmaceutical (non-packed powders) solids, one of the critical processing steps is the blending and mixing of the active pharmacological ingredient(s) with that of the inactive non-pharmacological ingredient(s) in a blender or mixer tank. Before further processing steps are undergone for this pharmaceutical product, blended powder samples are taken in order to be analyzed by the quality control department in order to determine if the active ingredients have been blended properly and are uniformly distributed within the blended powder. Such a test is called a blend uniformity analysis test or a homogeneity test. This procedure is referred to as "Process Validation" which requires pharmaceutical manufacturers to show proper control of the manufacturing process of any pharmaceutical drug. One of the requirements is to show evidence of proper blending of pharmaceutical actives and excipients. After the actives and excipients (non-active ingredients) are blended together in a blender, samples are taken from different sections of the blend and analyzed for proper distribution of the active ingredients.

In order to achieve proper information, the sample size should range from 1 to 3 times the mass of one unit dose. The sampled material should be representative of the blended pharmaceutical. Since the mass of one unit dose varies considerably from formula to formula, a single unit dose sampler with a nonadjustable sample volume would require multiple samplers.

In addition, since the size of blenders vary considerably with the added problem of limited clearance, the necessity of multiple samples, along with the requirement of assuring that the sampler can be thoroughly cleaned between sampled pharmaceuticals, would require pharmaceutical manufacturers to invest heavily in multiple samplers.

There remains a need for a rotatable batch sampling device having a wedge-shaped cone tip and a center section cut-out area for inserting into a dry powder blend that verifies the proper distribution of the active pharmacological ingredients, and enables the withdrawing of multiple precise samples of varying volumes without appreciably disturbing the powder blend matrix or the composition of the matrix when sampling, in order to insure accurate quality control testing. This must be done without appreciably disturbing the powder blend matrix when sampling. Thus verifying the proper distribution of the active pharmacological ingredients. Additionally, the sampling device must have the capability of taking a plurality of precise samples simultaneously of the dry blended powder at various depths by utilizing sampling cups having varying sample volumes.

DESCRIPTION OF THE PRIOR ART

Sampling devices, sampling tools, sampling probes, sample measuring apparatus, pellet samplers for the collecting and sampling of food grains, pharmaceutical powder blends, pellets, gases, soils, liquids and the like having various designs, structures, configurations, functions and materials of construction have been disclosed in the prior art. For example, U.S. Pat. Nos. 5,440,941 and 5,337,620 to KALIDINDI disclose a multiple-sampling device to obtain volumetric samplings of pharmaceutical powders, foods, ointments, cosmetic creams, emulsions and the like. The sampling device includes a plurality of dies having differently sized cavities (dependent upon the application of use) having die receiving means which are generally rod-shaped cylindrical bars with multiple interengageable portions. The sampling device further includes a sample access means in the form of a hollow-shaped tube with one open end and one tapered end. This prior art patent does not disclose the design, structure and configuration of the present invention.

U.S. Pat. No. 4,790,198 to AWTRY discloses a grain probe for sampling of grain kernels from grain storage facilities such as granaries, grain silos, grain bins or the like. The grain probe includes an inner tubular member mounted within an outer tubular member with the tubular members having openings formed therein which may be moved into registering alignment so that grain may enter the interior area of the inner tubular member. This prior art patent does not disclose the design, structure and configuration of the present invention.

U.S. Pat. No. 4,283,946 to BOWSER et al discloses a sampling probe for granular material from bulk storage facilities. The sampling probe includes a pair of coaxial elongated outer and inner sampling tubes which are rotatable relative to each other. The outer tube has a plurality of aligned openings for collecting the sample of the granular material. This prior art patent does not disclose the design, structure and configuration of the present invention.

None of these prior art patents teach or disclose the use of a multi-compartmentalized sampling device for simultaneously obtaining multiple samples without disturbing the powder blend matrix of sample material having the functionality, design, structure and configuration of the present invention.

Accordingly, it is an object of the present invention to provide a rotatable batch sampler having a wedge-shaped cone tip, a center section cut-out area and a wedge-shaped rear cut-out area for inserting into a dry powder blend without disturbing the powder blend matrix when sampling in order to obtain a proper distribution of the active pharmacological ingredients for accurate quality control testing of the sample material.

Another object of the present invention is to provide a rotatable batch sampler for taking multiple and precise samples simultaneously of the dry powder blends at various depths by utilizing sampling cups having varying sample volumes.

Another object of the present invention is to provide a rotatable batch sampler of varying lengths having multiple sampling cups that enables the procurement of dry powder blend samples without disturbing of the powder blend matrix for obtaining accurate quality control samples from very large blenders, mixers, tote bins, drums, fiber containers, silos, and the like.

Another object of the present invention is to provide a rotatable batch sampler that can be used in taking samples for agricultural products such as grains; for food industry products such as blended dry cheese powders; and for chemical processing industry products such as powder cements, dry blended ice-melters (salts) and the like.

Another object of the present invention is to provide a rotatable batch sampler having a wedge-shaped cone tip at the end of the batch sampler which allows the batch sampler to slide through a given section of the dry powder blend being sampled without appreciably altering the composition matrix of the constituent ingredients.

Another object of the present invention is to provide a rotatable batch sampler that has sampling cups wherein the size can be varied for allowing the collection of varying amounts of the dry powder blend that approximates 1 to 3 times a single unit dose amount of the pharmaceutical product.

Another object of the present invention is to provide a rotatable batch sampler that allows the simultaneous collection of up to five samples from various sections within the dry powder blend matrix of the batch being sampled.

Another object of the present invention is to provide a rotatable batch sampler having sampling cups that each rotate into and isolate a section of the dry powder blend matrix when the sample is being taken within the batch being sampled, such that the sampled section of the dry powder blend does not flow or fall into the batch sampler, thus preventing and eliminating any segregation of the active and inactive ingredients of the pharmaceutical product caused by the movement of the sampled material into the sampler.

Another object of the present invention is to provide a rotatable batch sampler having dual tapered cut-outs within the batch sampler, wherein the first tapered cut-out is located at the end of the batch sampler in the form of a wedge-shaped cone tip and the second tapered cut-out is located just above the center cut-out area (sampling area) in the form of a wedge-shaped cone section (being 180° degrees apart from each other). These dual tapered cut-outs are used for balancing the force on the batch sampler as it is inserted into the dry powder blend such the dual tapered cut-outs help prevent the batch sampling probe from wandering as it is inserted into the dry powder blend matrix in order to prevent disturbing the dry powder blend matrix being sampled.

Another further object of the present invention is to provide a rotatable batch sampler that can be mass produced in an automated and economical matter and is readily affordable by the user.

SUMMARY OF THE INVENTION

The present invention provides for a rotatable sampling device for obtaining at least one sample of a dry powder blended material from the powder blend matrix within a container. The sampling device includes a sample collection member, an insert rod member and a sampler extension member. The sample collection member includes a substantially tubular housing having a front section, a middle section and a rear section. The front section includes a tapered wedge-shaped cone tip for inserting into the blend matrix to be sampled. The middle section includes a center wedge-shaped section for use in the collection of at least one sample of the blend matrix; and the center wedge-shaped section further includes at least one interior insert chamber for receiving in each a sample collection cup for collecting a sample of the blend matrix. The rear section includes a tapered wedge-shaped cone section for preventing the sampling device from moving relative to the Z axis as the sampling device is inserted within the blend matrix. The sample collection member also includes the insert rod member for rotating at least one sample collection cup within at least one interior insert chamber.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein:

FIG. 10 is a partial cross-sectional perspective view of the rotatable batch sampler device of the present invention showing the sampler collection member having a tapered wedge-shaped cone tip, center cut-out section, the insert rod member, the interior insert chamber having a sample collection cup therein and a plate cover for receiving the sample collection cup therethrough;

FIG. 11 is a top perspective view of the rotatable batch sampler device of the present invention showing the sample collection cup and a section of the insert rod member therein;

FIG. 12 is a side perspective view of the rotatable batch sampler device of the present invention showing the sample collection cup and a section of the insert rod member therein;

DETAILED DESCRIPTION OF THE PREFERRED AND ALTERNATE EMBODIMENTS

OVERVIEW

Figure 1:
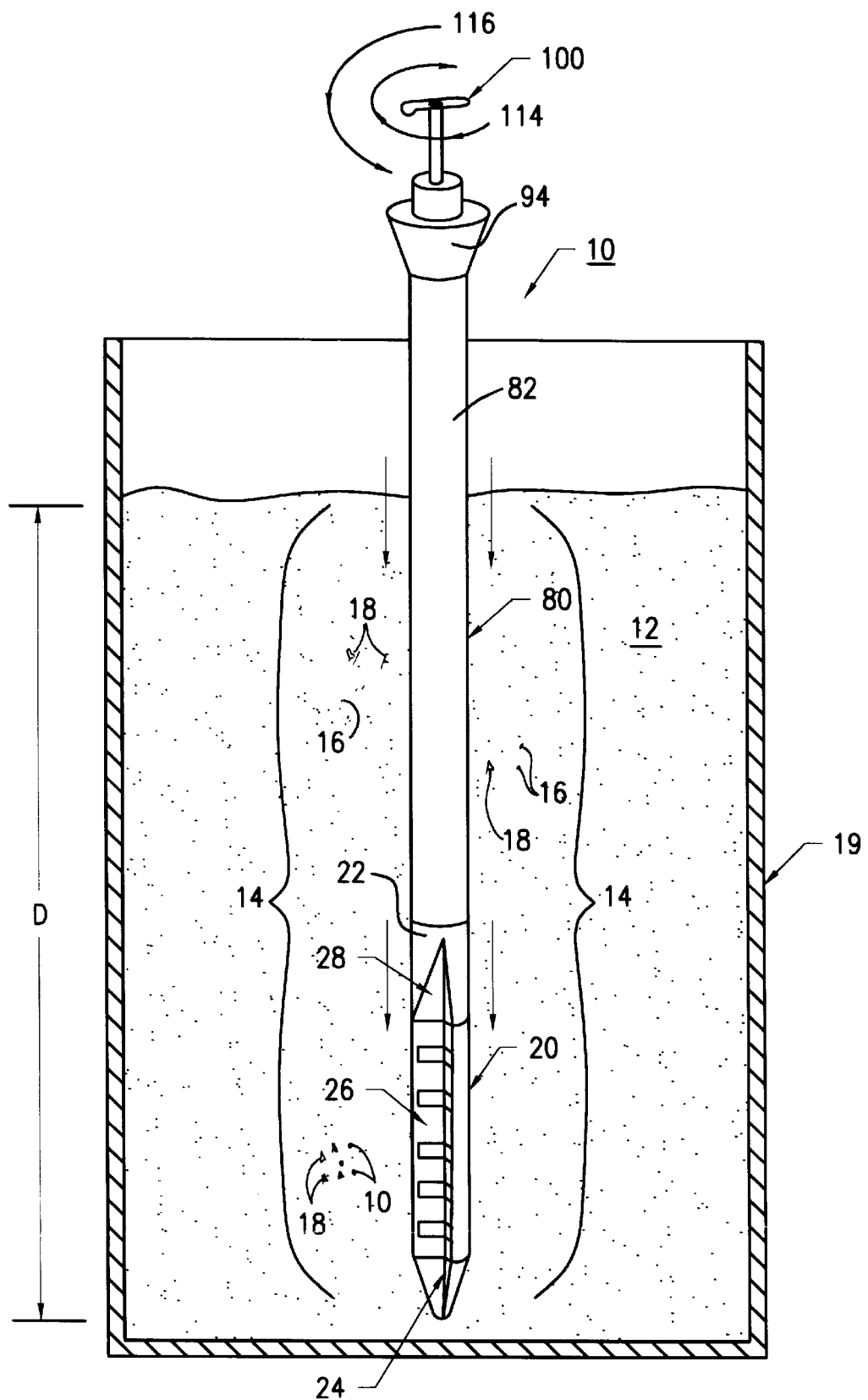
FIG. 1 is a front perspective view of the rotatable batch sampler device of the preferred embodiment of the present invention showing the major component parts therein, and in an assembled state for operational use thereof.

The rotatable batch sampler devices 10 and 200 and their component parts of the preferred and alternate embodiments of the present invention are represented in detail by FIGS. 1 through 15 of the drawings. The manual rotatable batch sampler device 10 of the preferred embodiment of the present invention, as shown in FIGS. 1 through 12 of the drawings, is a portable and manually used unit for inserting into a dry powder blend 12 without appreciably disturbing the powder blend matrix 14 or the composition of the matrix 14 for simultaneously obtaining multiple samples 15 from the powder blend matrix 14 of the pharmaceutical material 12 being sampled. This sampling is done in order to show a proper distribution of the active and inactive pharmacological ingredients 16 and 18 within the dry powder blend 12 for accurate quality control testing of the sample material 12.

Figure 13:
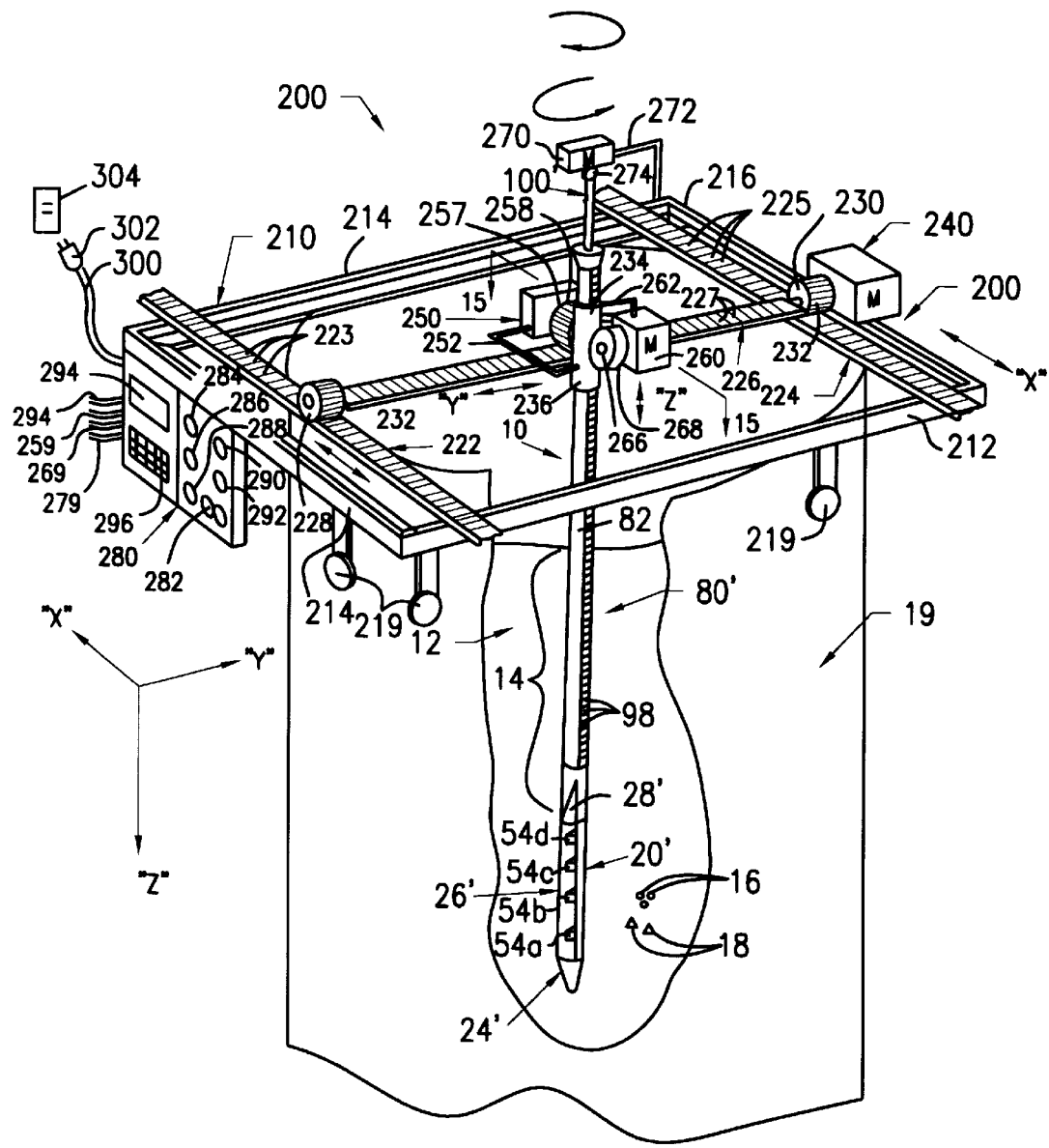
FIG. 13 is a perspective view of the rotatable batch sampler device of the alternate embodiment of the present invention showing the major component parts therein, and in an assembled state for operational use thereof.
Figure 14:
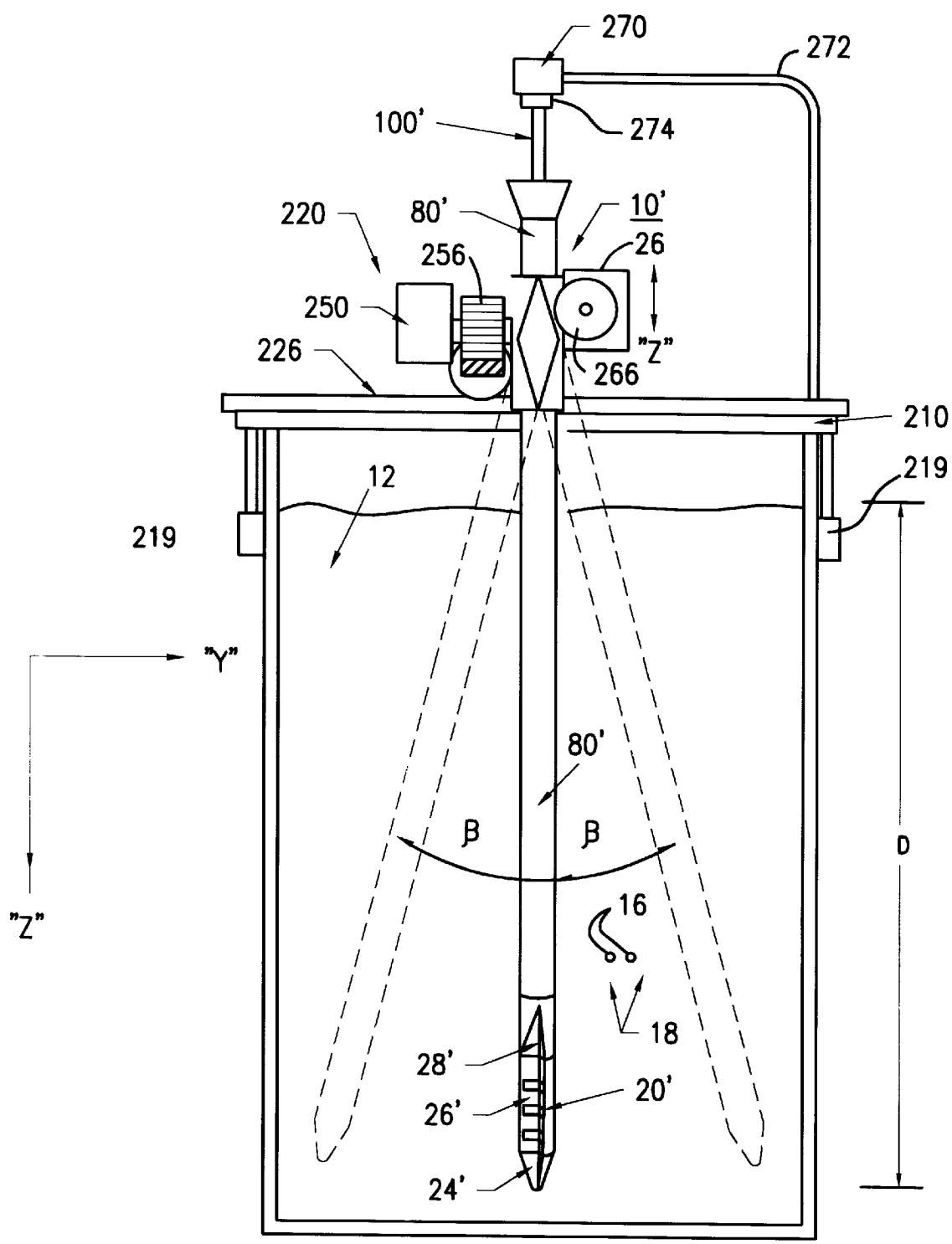
FIG. 14 is a side elevational view of the rotatable batch sampler device of the alternate embodiment of the present invention showing the motor for vertically inserting the sampler device into the dry powder blend matrix.
Figure 15:
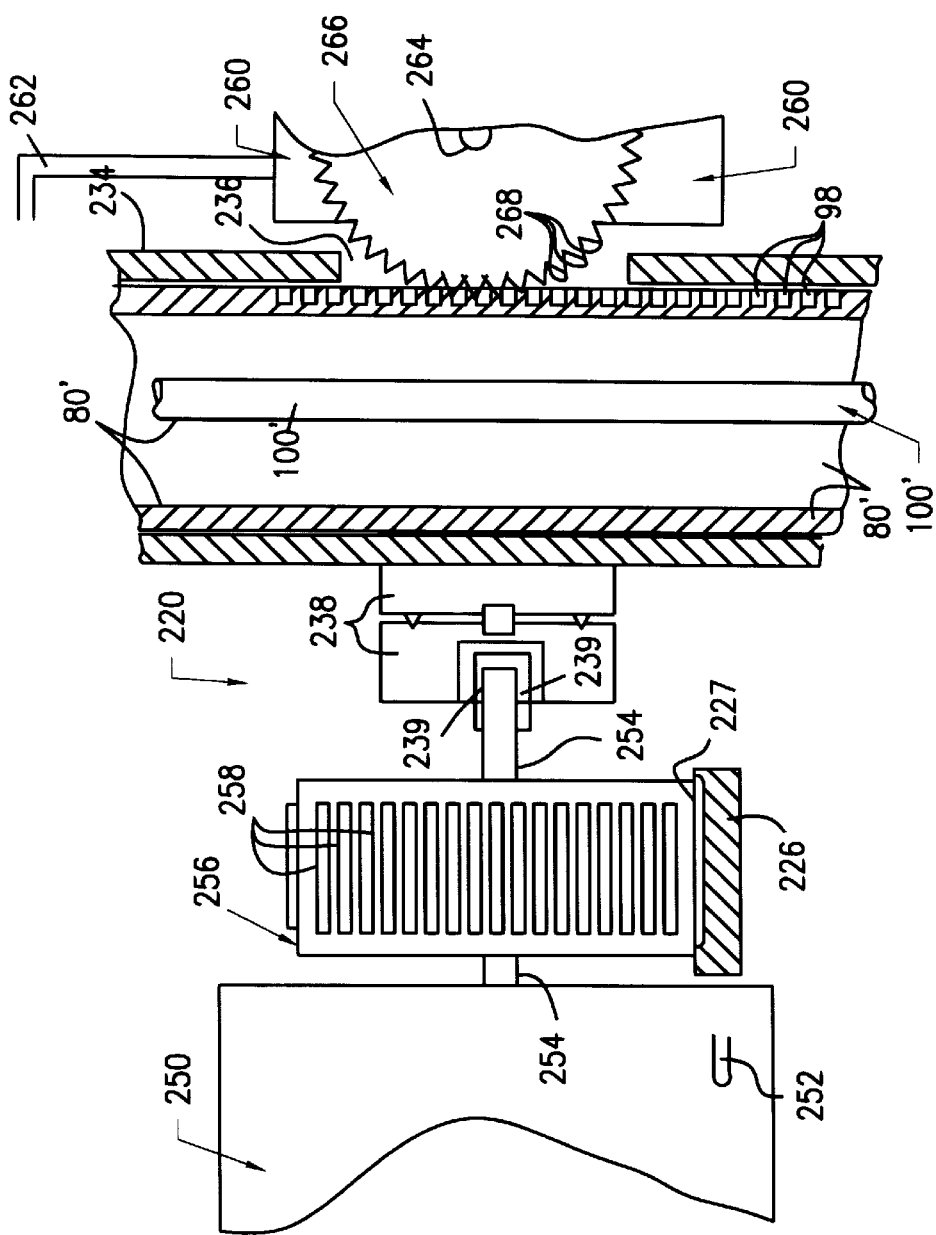
FIG. 15 is a cross-sectional view of the rotatable batch sampler device of the alternate embodiment of the present invention taken along lines 15—15 of FIG. 13 showing the servomotors, the sprocket gears, the ratchet plate member, the center tracking bar, and the sampler extension member in relationship to the collar member of the adjustable frame assembly.

The automated rotatable batch sampler device 200 of the alternate embodiment of the present invention, as shown in FIGS. 13 through 15 of the drawings, is a portable, programmable and automatic unit used in the pre-programmed sampling (multiple samples are taken automatically) of the dry powder blend 12 at various depths and location points within the dry powder container 19, mixer or blender. The sampling device 10 or 200 can be used in taking powder samples from different sized containers 19 that are intended to include blenders, silos, mixers, tote bins, pails, drums, fiber containers, vats and the like. The automatic rotatable batch sampler device 200 includes an adjustable frame assembly 210, a carriage assembly 220 having a first motor 240 for vertically inserting and pushing downwardly the sampler collection member 20 and the attached sampler extension member 80 through the powder blend matrix 14 to a given depth, as shown in FIG. 14 of the drawings; and a second electrical servomotor 260 for automatically turning the insert rod member 100 for collecting the multiple samples 15 from the powder blend matrix 14. In all other respects, the automatic rotatable batch sampler device 200 of the alternate embodiment is structurally the same as device 10, except for the addition of the adjustable frame assembly 210 and the carriage assembly 220 having the various electronic components attached thereto, such that device 200 functions and operates in the same manner as the manually operated rotatable batch sampler device 10 of the preferred embodiment.

Preferred Embodiment 10

The manually operated rotatable batch sampler device 10 and its component parts of the preferred embodiment of the present invention are represented in detail by FIGS. 1 to 12 of the drawings. The batch sampler device 10 includes a sampler collection member 20 connected to a sampler extension member 80, an insert rod member 100 for turning a plurality of sample collection cups 54a to 54e within the sampler collection member 20 for collecting two or more samples 15 from the dry powder blend matrix 14 when taking samples from the pharmaceutical product material 12, and a protective cover member 120.

The sampler collection member 20 includes a substantially cylindrical tubular housing 22 made of metals such as stainless steel or aluminum, or moldable and durable plastics for ease of cleaning and maintenance. Housing 22 includes a front section 24 in the form of a tapered wedge-shaped cone tip for inserting into the powder blend matrix 14, a middle section 26 in the form of a center cut-out wedge-shaped section being used for the collection of multiple samples 15, and a rear section 28 in the form of a tapered wedge-shaped cut-out cone section for balancing and preventing the batch sampler device 10 from wandering as it is inserted within the powder blend matrix 14.

Figure 2:
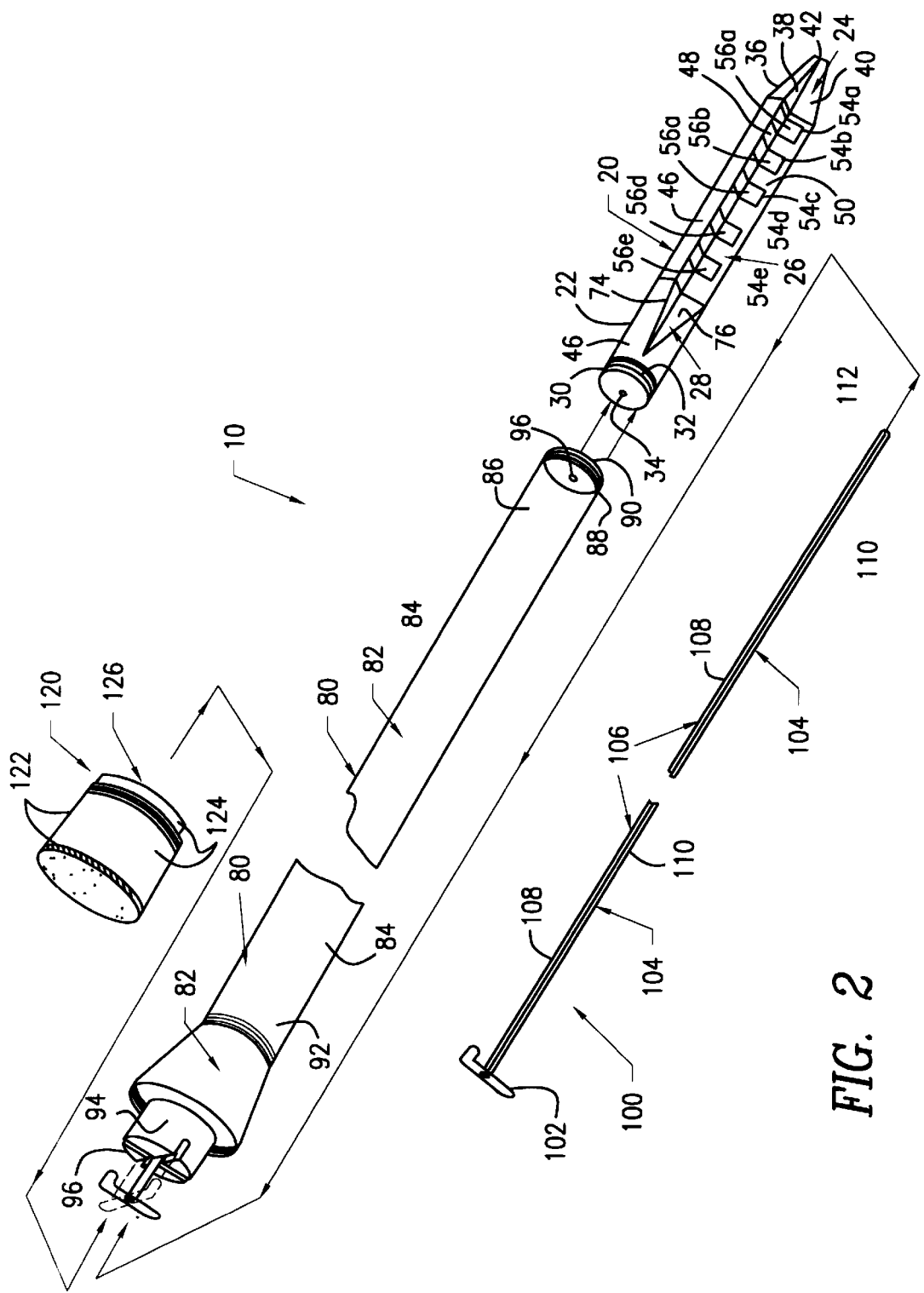
FIG. 2 is an exploded perspective view of the rotatable batch sampler device of the present invention showing the sampler collection member having a tapered wedge-shaped cone tip, and a plurality of sample collection cups therein, the sampler extension member having a rod insert component thereon, the rod insert member, and the protective cap cover.
Figure 8:
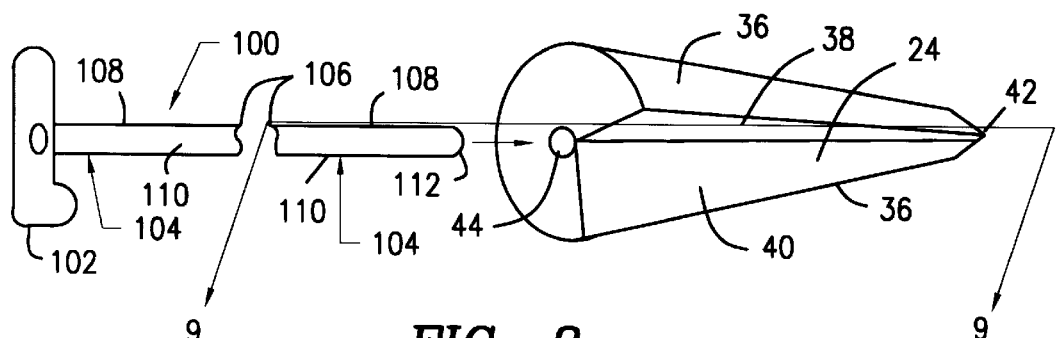
FIG. 8 is a front sectional perspective view of the rotatable batch sampler device of the present invention showing the insertion of the rod insert member into the hole opening within the tapered wedge-shaped cone tip of the sampler collection member.
Figure 9:
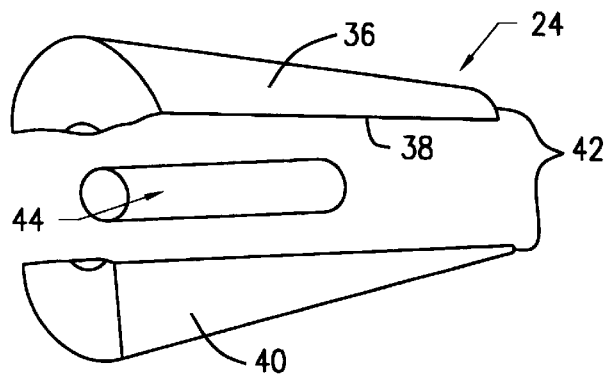
FIG. 9 is a cross-sectional perspective view of the rotatable batch sampler device of the present invention taken along lines 9—9 of FIG. 8 showing the locking mechanism of the rod insert member with the hole opening within the tapered wedge-shaped cone tip of the sampler collection member.

Cone tip 24 includes an outer wall surface 36, a pair of inner wall surfaces 38 and 40 and a cone-end point 42 for engaging and piercing through powder blend matrix 14 as the batch sampler device 10 is pushed downward into the powder blend matrix 14, as shown in FIG. 1 of the drawings. Cone tip 24 also includes an opening 44 having a semi-circular shaped-hole 44sc for locking with the insert rod member 100, as shown in FIGS. 8 and 9 of the drawings. The angle $\alpha$ opening for the wedge-shaped cut-out sections 24, 26, and 28 between each of the inner wall surfaces 38 and 40, 48 and 50, and 74 and 76, respectively, as shown in FIG. 2 of the drawings, includes an overall range $\alpha$ of 90° to 150° for the angle opening, a preferred range $\alpha$ of 110° to 140° for the angle opening and having a specific angle opening wherein $\alpha$ is 120°. The sampler collection member 20 has a physical length measurement of between 12 inches, to 21 inches depending upon the number of sample collection cups 54a to 54e that are being used for sampling; and a diameter measurement between 1 and 6 inches, depending upon the type of material 12 being sampled.

Figure 4:
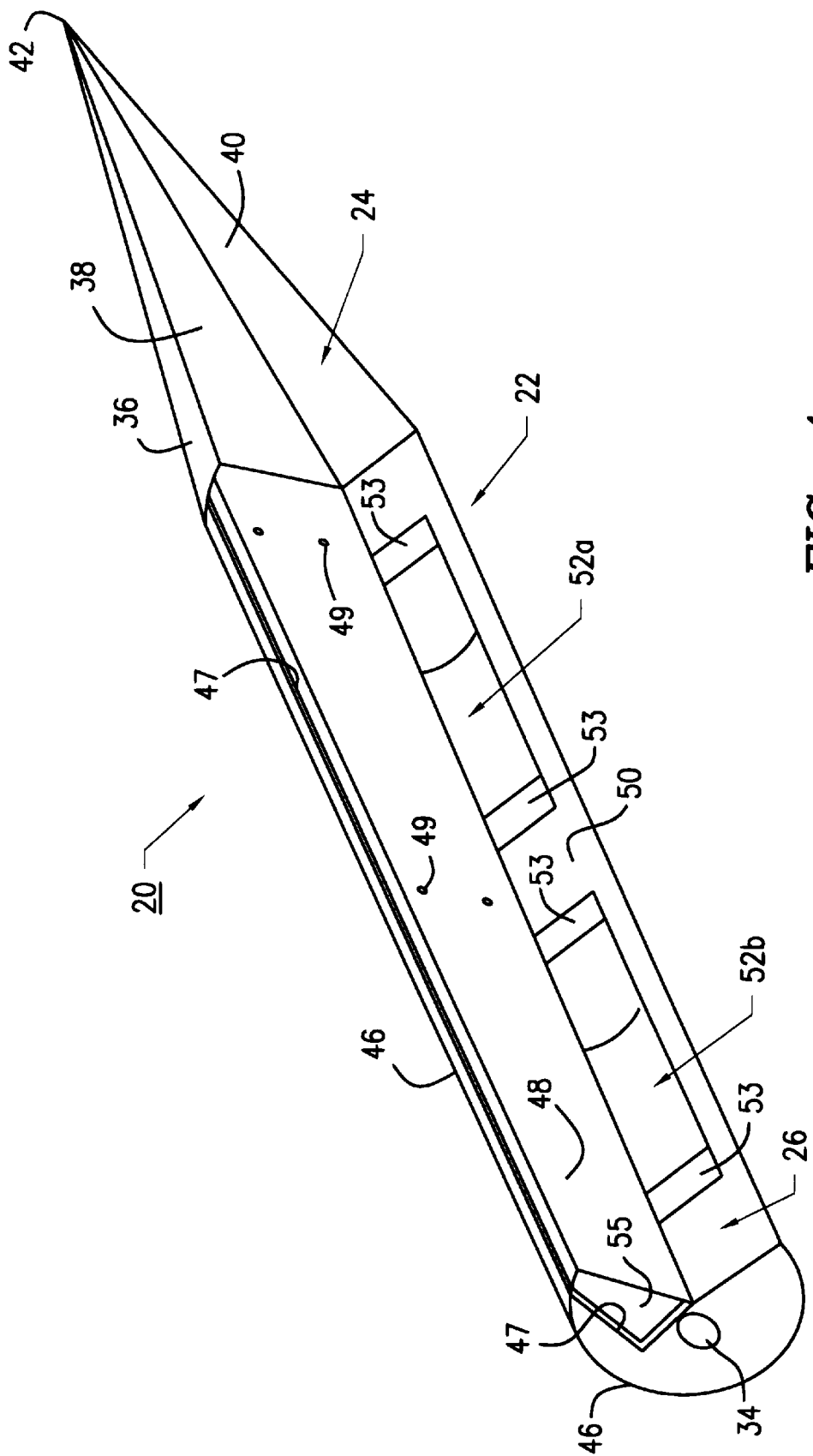
FIG. 4 is a front perspective view of the rotatable batch sampler device of the present invention taken along lines 4—4 of FIG. 3 showing the sampler collection member having a tapered wedge-shaped cone tip, and a center cut-out section having a plurality of sample collection cups therein.
Figure 4A:
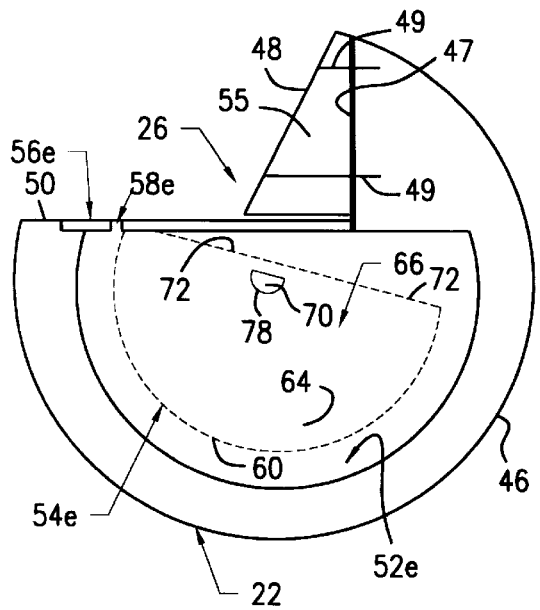
FIG. 4A is an enlarged cross-sectional view of the rotatable batch sampler device of the present invention taken along lines 4A—4A of FIG. 3 showing the sampler collection member having the collection cup interior insert chamber, the sampler collection cup, the plate cover for the sample collection cup, and the centrally located hole opening for inserting the rod insert member therein.

The center cut-out wedge-shaped section 26 includes an outer wall surface 46, a pair of inner wall surfaces 48 and 50 and a hole opening 34 for receiving therein the insert rod member 100, as shown in FIG. 10. The center cut-out wedge-shaped section 26 further includes a plurality of interior insert chambers 52a to 52e for receiving therein a plurality of sample collection cups 54a to 54e. Each interior insert chamber 52a to 52e also includes a recessed perimeter edge 53 for receiving therein plate covers 56a to 56e. Each of the sample collection cups 54a to 54e includes an outer semi-cylindrical wall 60 and a pair of side walls 62 and 64 for forming an interior compartment 66 for receiving a precise volumetric amount to form a sample 15 of the dry powder blend matrix material 14 therein. Each side wall 62 and 64 includes a semi-circular hole opening 68 and 70 having a semi-circular cylindrical holding member 78 therein, as shown in FIG. 11. Holding member 78 is welded to hole opening 68 and 70, respectively. Holding member 78 is used for receiving therein the insert rod member 100. Each sample collection cup 54a to 54e further includes an outer perimeter edge 72. Additionally, each of the interior insert chambers 52a to 52e has a plate cover 56a to 56e with a U-shaped opening 58a to 58e therein for receiving therethrough sample collection cups 54a to 54e, respectively. Plate covers 56a to 56e are attached to the perimeter edge 53 of the inner wall surface 50, as shown in FIGS. 3, 4, 4A and 6 of the drawings. The center cut-out section 26 also includes a triangular-shaped block component 55 of varying sizes for receiving thereon the leading perimeter edges 72 of each of the sample collection cups 54a to 54e, respectively, as depicted in FIG. 4 of the drawings. Block component 55 is attached to an interior inner wall surface 47 of the center cut-out section 26 via insert pins 49. Block component 55 acts as a stop to the sample collection cups 54a to 54e in the collecting of each of the powder blend samples 15 when the insert rod member 100 has been turned clockwise and locked in place.

Rear section 28 also includes a male connection member 30 having spiral threads 32 thereon for connecting the sampler extension member 80 thereto. The tapered wedge-shaped cut-out cone section 28 includes an outer wall surface 46 and inner wall surfaces 74 and 76, as depicted in FIGS. 1 and 2 of the drawings.

Figure 2A:
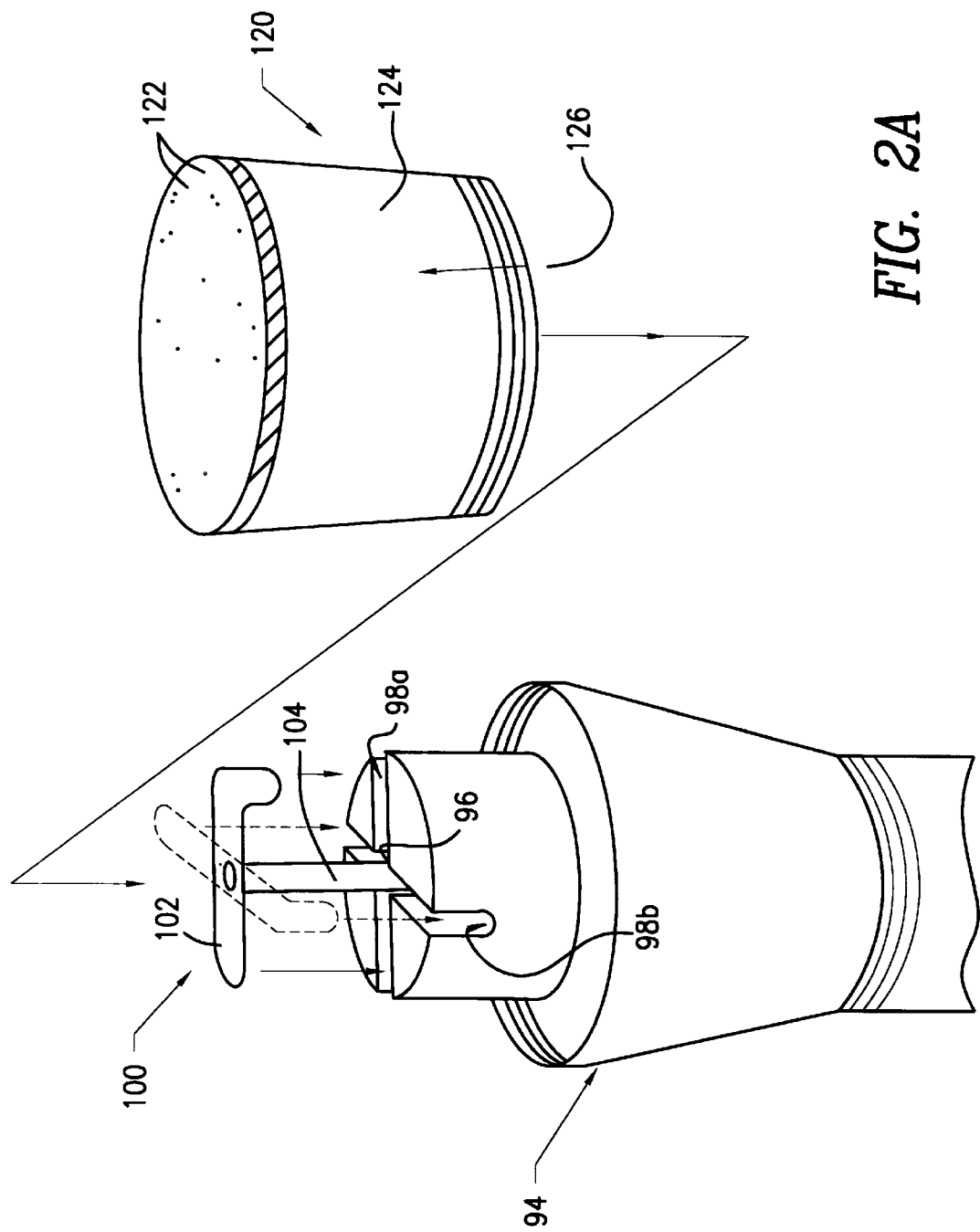
FIG. 2A is an enlarged perspective view of the rotatable batch sampler device of the preferred embodiment of the present invention showing the rod insert member within the rod insert component head of the sampler extension member, and the protective cover member being readied to cover the rod insert component head thereon.
Figure 3:
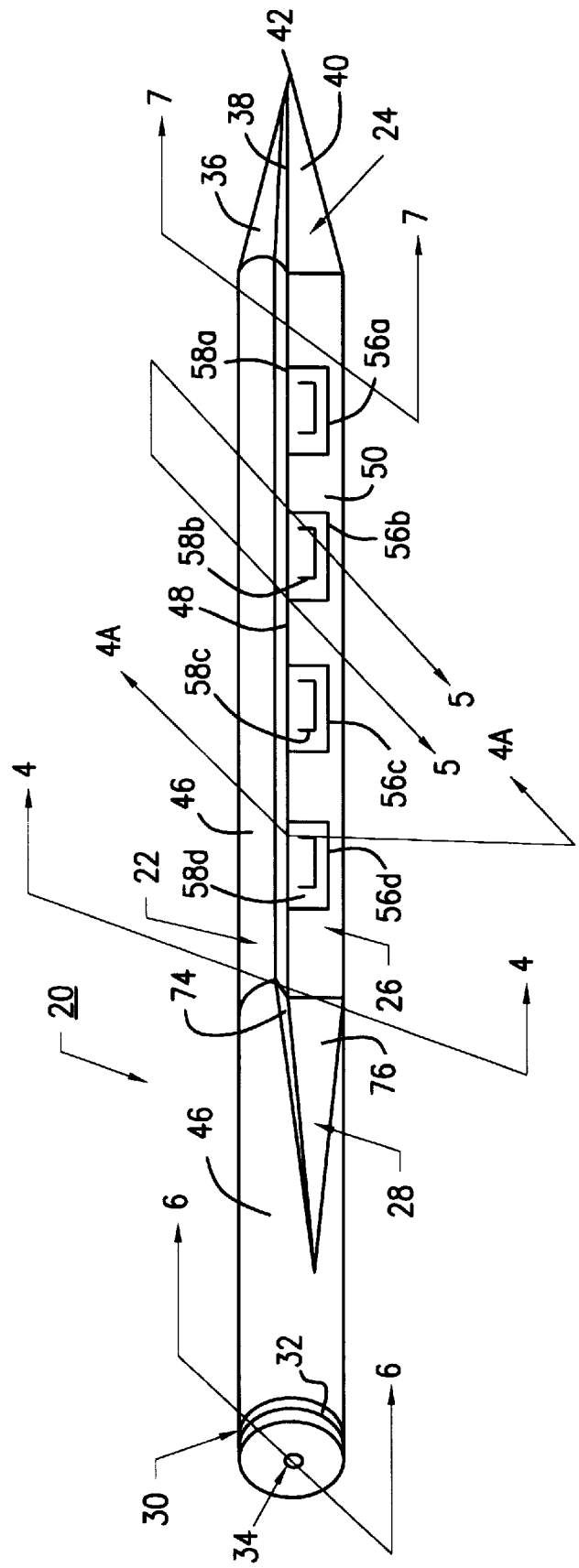
FIG. 3 is a front perspective view of the rotatable batch sampler device of the present invention showing the sampler collection member having a tapered wedge-shaped cone tip, a center cut-out section having a plurality of sample collection cups therein, a rear tapered wedge-shaped cut-out section and a centrally located hole opening for inserting the rod insert member therein.

The sampler extension member 80 includes a substantially cylindrical tubular housing 82 made of metals such as stainless steel or aluminum, or moldable and durable plastics for ease of cleaning and maintenance having an outer wall surface 84. The sampler extension member 80 is used for extending the total length of the sampler device 10 depending upon the height of container 19, as depicted in FIG. 1. The sampler extension 80 further includes at one end 86 a female connection member 88 having spiral threads 90 therein for connecting to the male connection member 30 of the sampler collection member 20; and at the other end 92 a rod insert component head 94 having a hole opening 96 therethrough for receiving the insert rod member 100. Component head 94, as shown in FIG. 2A, also includes a pair of U-shaped receiving channels 98a and 98b for receiving therein handle member 102 of insert rod member 100, such that the sample collection cups 54a to 54e are ready to be rotated for collecting a sample 15 from a blend matrix 14 (i.e. handle member 102 is in receiving channel 98a); or the sample collection cups 54a to 54e have been rotated to a closed position via rod insert member 100 with the sample collection cups 54a to 54e capturing multiple samples 15 therein (i.e. handle member 102 is in receiving channel 98b) of the blend matrix 14. The sampler extension member 80 has a physical length measurement between 12 inches to 60 inches depending upon the type of container 19 the pharmaceutical material 12 or other types of blended products (such as grains) are contained therein; and a diameter measurement of between 1 and 6 inches.

Insert rod member 100 includes a handle member 102 and an attached rod component 104 having a semi-cylindrical shape 106 with a flat wall surface 108 and a curved wall surface 110; and having a rod tip 112. Insert rod member 100 is inserted through hole openings 96, 34 and 44 of the sampler extension member 80, the sampler collection member 20 and cone tip 24, respectively. The insert rod member 100 is then turned in a clockwise direction 114 such that the plurality of sample collection cups 54a to 54e capture a precise amount of pharmaceutical product material 12 within each of the cups 54a to 54e of the dry powder blend matrix 14 without disturbing the powder blend matrix 14 when the samples were being taken. The insert rod member 100 has physical length measurements of the attached rod component 104 of between 10 inches to 58 inches; and a diameter of the semi-cylindrical rod shape 106 between ¼ inch to ½ inch.

The protective cap member 120, as shown in FIG. 2, includes a reinforced top wall 122, a cylindrical side wall 124 for forming an interior area 126 in the shape of the rod insert component head 94 of the sampler extension member 80. Cap member 120 is used for protecting the rod insert component head 94 from damage when the user is hammering the reinforced top wall 122 of the cap member 120 when manually inserting the rotatable batch sampler device 10 into the powder blend matrix 14.

An additional use of the present invention is for the sampling of grains (wheat, barley, milled corn, etc.) in grain silos, as previously mentioned. Extension member 80 can be made of any suitable length for this purpose. Also, if necessary, extension member 80 may be made in a plurality of sections to achieve the desired length. Likewise, insert rod member 100 can also be made of any suitable length for this grain sampling purpose. Also, if necessary, insert rod member 100 may be made in a plurality of sections to achieve the desired length.

Alternate Embodiment 200

The automatically operated rotatable batch sampler device 200 and its component parts of the alternate embodiment of the present invention are represented in detail by FIGS. 13, 14 and 15 of the drawings. The automated rotatable batch sampler device 200 includes an adjustable frame assembly 210 for mounting and attaching to various types of blenders, mixers, containers 19, silos and the like, having thereon a plurality of mounting means in the form of clamps, fasteners, suction clamps 219 for attaching the adjustable frame assembly 210 to the aforementioned containers 19. The automated rotatable batch sampler device 200 further includes a carriage assembly 220 having a series of electric motors 240, 250, 260 and 270 for manipulating the batch sampler device 10' in the "X", "Y" and "Z" directions, as depicted in FIGS. 13 and 14 of the drawings. Additionally, the automated rotatable batch sampler device 200 also includes a programmable electronic controller/control panel 280 for controlling the manipulation of the batch sampler device 200 in the "X", "Y" and "Z" directions, via electric motors 240, 250, 260 and 270. In all other respects, the batch sampler device 200 of the alternate embodiment, functions and operates in a similar manner to the batch sampler device 10 of the preferred embodiment.

The adjustable frame assembly 210 includes adjustable and expandable L-shaped front, rear, and side bars 212, 214, 216 and 218. Each L-shaped bar 212, 214, 216 and 218 includes one or more L-shaped sections (not shown) that are adjustable and expandable such that the assembled frame assembly 210 properly fits on a variety of differently sized containers 19, mixers, blenders, silos and the like for operational use. Frame assembly 210 can be made from lightweight metals or from durable and rigid plastics. Carriage assembly 220 includes adjustable and expandable side tracking bars 222 and 224 having tracking recesses/channels 223 and 225 therein, and an adjustable and expandable center tracking bar 226 having tracking recesses/channels 227 therein. Each end of tracking bar 226 includes an attached sprocket gear 228 and 230 having sprocket tabs 232 thereon, as depicted in FIG. 13 of the drawings. Each tracking bar 222, 224 and 226 includes one or more sections (not shown) that are adjustable and expandable, such that these tracking bars 222, 224 and 226 conform to the adjusted width and length of the fully formed and assembled frame assembly 210, as shown in FIGS. 13 and 14 of the drawings. Sprocket tabs 232 on each of the sprocket gears 228 and 230 track within each of the tracking recesses/channels 223 and 225 of tracking bars 222 and 224, respectively, such that when electrical servomotor 240 is operational, sprocket gears 228 and 230 can move on the tracking bars 222 and 224 along the "X" axis, as depicted in FIG. 13 of the drawings. Additionally, carriage assembly 220 also includes a collar member 234 having a rectangular opening 236 therein. Collar member 234 is slidably connected to the sampler extension member 80'. Collar member 234 has attached thereon electrical servomotors 250 and 260 via adjustable U-shaped brackets 252 and 262, respectively. Servomotor 250 includes a shaft 254 having thereon a sprocket gear 256 having sprocket tabs 258 attached thereto; such that sprocket tabs 258 on sprocket gear 256 engage and track within tracking recesses/channels 227 of center tracking bar 226, where then sprocket gear 256 can move on the tracking bar 226 via motor 250 along the "Y" axis, as depicted in FIGS. 13 and 15 of the drawings. Servomotor 260 includes a shaft 264 having thereon a sprocket gear 266 having sprocket tabs 268 attached thereto. The sprocket tabs 268 on sprocket gear 266 engage and track within the rectangular opening 236 of collar member 234 in which sprocket tabs 268 move onto the plurality of rectangularly-shaped recessed openings 98 located along the vertical length/"Z" axis of the tubular housing 82 of sampler extension member 80' via motor 260, as depicted in FIGS. 13, 14 and 15 of the drawings. Additionally, collar member 234 further includes an attached rachet plate member 238 having a ball bearing component 339 for shaft 264 for enabling the batch sampler device 200 to be angled (angle β) up to a 60° degree angle from the "Z" axis, as depicted in FIGS. 14 and 15 of the drawings. Carriage assembly 220 can be made from lightweight metals or from durable and rigid plastics.

Servomotor 270 is connected to the adjustable frame assembly 210 via adjustable U-shaped bracket 272. Servomotor 270 is directly connected to the insert rod member 100' via a spring component 274 in which to lock the insert rod member 100' within the cone tip 24' when the servomotor 270 has been activated in turning the plurality of sample collection cups 54a' to 54e' to capture and collect multiple samples 15 from the powder blend matrix 14 of the pharmaceutical material 12 being analyzed.

The programmable electronic controller/control panel 280 is electrically connected to each of the servomotors 240, 250, 260 and 270 via electrical lines 249, 259, 269 and 279. The programmable control panel 280 is used for controlling the servomotors 240, 250 and 260 in positioning the batch sampler device 200 with respect to precise locations along the "X", "Y" and "Z" axis; for turning the insert rod member 100' via servomotor 270 in a clockwise fashion; and for powering the servomotors 240, 250, 260 and 270, respectively. Control panel 280 includes a plurality of control members 282, 284, 286, 288, 290 and 292; a visual display screen 294 having a keyboard 296 for programming the aforementioned output functions of positioning the sampler device 200 along specific points on the "X", "Y" and "Z", for turning the insert rod member 100' and for powering up the servomotors 240, 250, 260 and 270, respectively; and an electrical cord 300 having a plug 302 for connecting to a power source 304. The control members include an ON/OFF button 282 for activating and de-activating the aforementioned servomotors 240, 250, 260 and 270; a control knob/selector 284 for moving sprocket gears 228 and 230 on tracking bars 222 and 224, respectively, via servomotor 240 along the "X" axis; a control knob/selector 286 for moving sprocket gear 256 on tracking bar 226 via servomotor 250 along "Y" axis; a control knob/selector 288 for moving sprocket gear 266 on the plurality of openings 98 on the sampler extension member 80' via motor 260 in order to control the depth of the batch sampler device 200 along the "Z" axis; a control knob/selector 290 for selecting an angle β in moving and angling the batch sampler device 200 along the "Z" axis via the rachet plate component 238 and the servomotor 250; and a control knob/selector 292 for turning the insert rod member 100' in a clockwise manner in order to capture multiple samples 15 within the powder blend matrix 14.

Operation of the Present Invention

Figure 5:
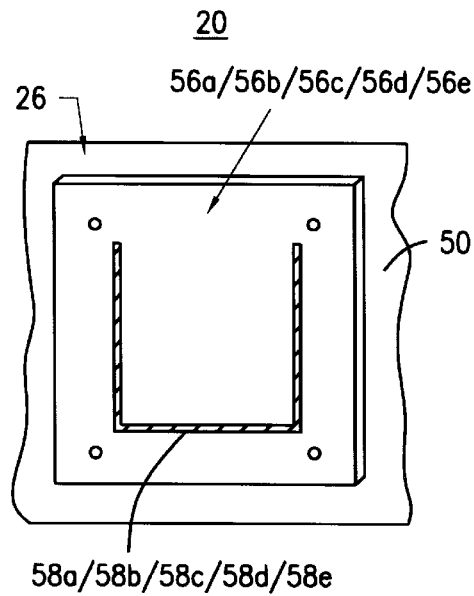
FIG. 5 is a sectional front view of the rotatable batch sampler device of the present invention taken along lines 5—5 of FIG. 3 showing the sampler collection member having the plate cover with a U-shaped opening for receiving therethrough the sample collection cup being located on the center cut-out section for covering the collection cup interior insert chamber.
Figure 6:
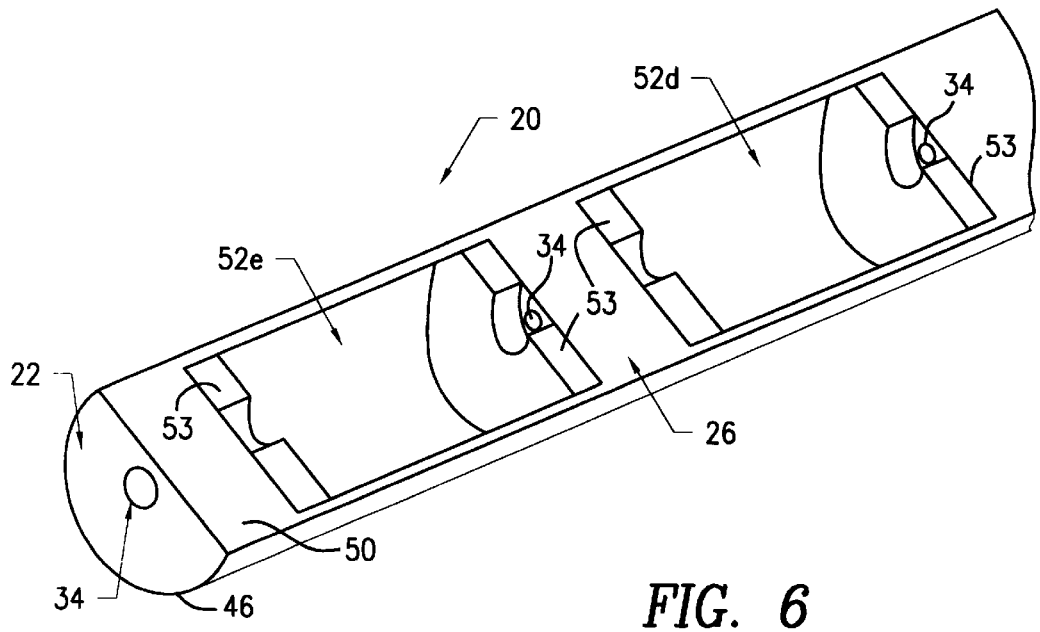
FIG. 6 is a cross-sectional top view of the rotatable batch sampler device of the present invention taken along lines 6—6 of FIG. 3 showing the sampler collection member having a plurality of collection cup interior insert chambers being located on the center cut-out section for receiving therein a collection cup and the centrally located hole opening for receiving therein the rod insert member.
Figure 7:
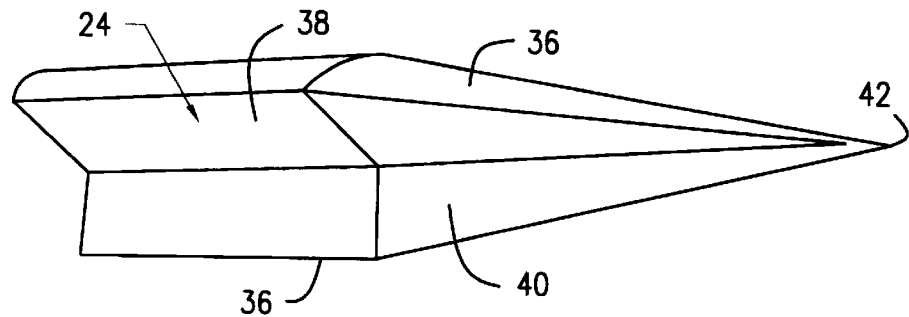
FIG. 7 is a front sectional perspective view of the rotatable batch sampler device of the present invention taken along lines 7—7 of FIG. 3 showing the sampler collection member having the tapered wedge-shaped cone tip for inserting into the dry powder blend matrix.

In operating the manual rotatable batch sampler device 10 of the preferred embodiment of the present invention, the user first assembles the clean component parts of the sampler device 10, as depicted in FIG. 2 of the drawings. The user attaches the sampler collection member 20 to the sampler extension member 80 such that the male connection member 30 of the sampler collection member 20 is threadedly connected to female connection member 88 of the sampler extension member 80, as shown in FIG. 1 of the drawings. The insert rod member 100 is inserted into the aligned openings 96, 34 and 44, respectively, and rod member 100 is then turned in a counter-clockwise direction 116 in order to insure that the plurality of sample collection cups 54a to 54e are positioned within the interior insert chambers 52a to 52e and behind each of the plurality of cover plates 56a to 56e that cover each of the interior insert chambers 52a to 52e, as depicted in FIGS. 1, 4 and 5 of the drawings. The insert rod member 100 is covered and held in place with the protective cap member 120 for covering and protecting the rod insert component head 94.

The user now selects a particular location on the surface of the pharmaceutical material 12 being sampled from within the blender, mixer, container 19 or the like, such that the user pierces the surface of product material 12 and pushes downwardly or hammers the protective cap member 120 downwardly by using the tapered wedge-shaped cutout cone tip 24. Then the cut-out areas at the cone tip 24, middle section 26, and rear section 28 of the sampler collection member 20 allow sampling device 10 to move through the powder blend matrix 14 of the batch product material 12 being sampled without appreciably altering the composition of the active and inactive ingredients 16 and 18 within the powder blend matrix 14, and with only minimal disturbance of the blend matrix, as shown in FIG. 1 of the drawings.

The user having selected a particular depth D of insertion for the sampler collection member 20 and the attached sampler extension member 80 of sampler device 10, as shown in FIG. 1, the user is now ready to capture and collect multiple samples 15 within the powder blend matrix 14 via the plurality of sample collection cups 54a to 54e. The user now removes the protective cap member 120 from the insert component head 94, where then the user manually turns the insert rod member 100 in a clockwise direction 114. This rotatable movement results in the circular movement of sample collection cups 54a to 54e from behind the cover plates 56a to 56e through each of the U-shaped openings 58a to 58e in order to capture and collect the multiple samples 15 within the powder blend matrix 14. The insert rod member 100 when turned completely locks the rod tip 12 of the insert rod member 100 within the hole opening 44 of the cone tip 24, such that leading perimeter edges 72 of each of the sample collection cups 54a to 54e is stopped against the inner side wall 50 where a precise amount of the multiple powder blend samples 15 have been collected for constituent analysis. When the samples 15 have actually been taken, these sampling cups 54a to 54e have rotated into and isolate the section of the powder blend matrix 14 being sampled without appreciably disturbing the blend matrix 14 or the composition of the matrix 14 as the sampling cups 54a to 54e are rotated within the product material 12.

The user now pulls the extension member 80 in an upwardly direction and removes the entire batch sampler device 10 from the product material 12 within container 19. The user then lifts outwardly (a few inches) the rod tip 112 of the insert rod member 100 from hole opening 44 within cone tip 24. Then the user is ready to remove the contents of each sample cup 54a to 54e collectively after brushing off adhering particles. The user simply turns the rod member 100 counter clockwise 116 to open the sample collection cup samples 15 for quality control analysis of the samples material components. The aforementioned sampling procedure is repeated and is done at several locations and depths within the container 19 to ascertain if proper blending of the pharmaceutical active and inactive ingredients 16 and 18 have occurred within the product material 12.

When using the sampling device for the downward vertical insertion step, the sampler collection member 20 will not appreciably disturb the powder blend matrix 14 of the product material 12 or the composition of the matrix 14; and when the sampling cups 54a to 54e of the sampler collection member 20 are used for the rotation collection step, the sampling cups 54a to 54e are rotated via the insert rod member 100 to capture and collect multiple powder blend samples 15 within the blend matrix 14, such that there will be no appreciable altering of the composition's active and inactive pharmacological ingredients 16 and 18 within product material 12, and such that the matrix 14 is not appreciably disturbed.

In operating the automated rotatable batch sampler device 200 of the alternate embodiment of the present invention, the user first assembles the adjustable frame assembly 210 to properly fit the container 19 and then assembles the batch sampler device 200 as previously discussed for the batch sampler device 10 of the preferred embodiment. In adjusting the adjustable frame assembly 210 the user simply expands each of the adjustable L-shaped bars 212, 214, 216 and 218, as well as the expandable and adjustable tracking bars 222, 224 and 226 to fit on container 19, as depicted in FIGS. 13 and 14 of the drawings. Frame assembly 210 is firmly held in place by suction clamps 220, as shown in FIG. 13 of the drawings. The user now activates control panel 280 by plugging in electrical cord 300 and plug 302 to power source 304, where then the user depresses the control ON/OFF button 282 for powering up the programmable controller 280. The user now programs the programmable controller 280 via the display screen 294 having keyboard 154 for programming the output functions of control members 284, 286, 288 and 290 in which to position the sampler device 200 along specific points on the "X", "Y" and "Z", as well as for selecting an angle β for angling the sampler device 200 along the "Z" axis for a particular type of container 19 being sampled from. Control member 292 is activated when the sampler device 200 has reached its programmed coordinates along the "X", "Y" and "Z" and angle β positions in order for the multiple samples 15 of the powder blend matrix 14 to be collected via sample collection cups 54a to 54e, as shown in FIGS. 13 and 14 of the drawings. After the sampling is completed, control member 288 is depressed again for removing the batch sampler device 200 from the powder blend matrix 14 in which to remove the multiple samples 15 from the sample collection cups 54a to 54e, as previously described from batch sampler device 10 of the preferred embodiment. The batch sampler device 200 of the alternate embodiment operates and functions in a similar manner, as the batch sampler device 10 of the preferred embodiment.

The automated batch sampler device 200 can be preprogrammed to take several multiple samplings 15 at various positions and depths along the "X", "Y" and "Z" axes via control panel 280.

Advantages of the Present Invention

Accordingly, an advantage of the present invention is that it provides for a rotatable batch sampler having a wedge-shaped cone tip, a center section cut-out area and a wedge-shaped rear cut-out area for inserting into a dry powder blend without disturbing the powder blend matrix when sampling in order to obtain a proper distribution of the active pharmacological ingredients for accurate quality control testing of the sample material.

Another advantage of the present invention is that it provides for a rotatable batch sampler for taking multiple and precise samples simultaneously of the dry powder blends at various depths by utilizing sampling cups having varying sample volumes.

Another advantage of the present invention is that it provides for a rotatable batch sampler of varying lengths having multiple sampling cups that enables the procurement of dry powder blend samples without disturbing the powder blend matrix for obtaining accurate quality control samples from very large blenders, mixers, tote bins, drums, fiber containers, silos, and the like.

Another advantage of the present invention is that it provides for a rotatable batch sampler that can be used in taking samples for agricultural products such as grains; for food industry products such as blended dry cheese powders; and for chemical processing industry products such as powder cements, dry blended ice-melters (salts) and the like.

Another advantage of the present invention is that it provides for a rotatable batch sampler having a wedge-shaped cone tip at the end of the batch sampler which allows the batch sampler to slide through a given section of the dry powder blend being sampled without appreciably altering the composition matrix of the constituent ingredients.

Another advantage of the present invention is that it provides for a rotatable batch sampler that has sampling cups wherein the size can be varied for allowing the collection of varying amounts of the dry powder blend that approximates 1 to 3 times a single unit dose amount of the pharmaceutical product.

Another advantage of the present invention is that it provides for a rotatable batch sampler that allows the simultaneous collection of up to five samples from various sections within the dry powder blend matrix of the batch being sampled.

Another advantage of the present invention is that it provides for a rotatable batch sampler having sampling cups that each rotate into and isolate a section of the dry powder blend matrix when the sample is being taken within the batch being sampled, such that the sampled section of the dry powder blend does not flow or fall into the batch sampler, thus preventing and eliminating any segregation of the active and inactive ingredients of the pharmaceutical product caused by the movement of the sampled material into the sampler.

Another advantage of the present invention is that it provides for a rotatable batch sampler having dual tapered cut-outs within the batch sampler, wherein the first tapered cut-out is located at the end of the batch sampler in the form of a wedge-shaped cone tip and the second tapered cut-out is located just above the center cut-out area (sampling area) in the form of a wedge-shaped cone section (being 180° degrees apart from each other) These dual tapered cut-outs are used for balancing the force on the batch sampler as it is inserted into the dry powder blend such the dual tapered cut-outs help prevent the batch sampling probe from wandering as it is inserted into the dry powder blend matrix in order to prevent disturbing the dry powder blend matrix.

Another further advantage of the present invention is that it provides for a rotatable batch sampler that can be mass produced in an automated and economical matter and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A rotatable sampling device for obtaining at least one sample of a dry powder blended material from the powder blend matrix within a container, comprising:

a) a sampling device including a sample collection member, an insert rod member and a sampler extension member;

b) said sample collection member including a substantially tubular housing having a front section, a middle section and a rear section;

c) said front section including a tapered cone tip having a cut-out section defining a tapered wedge-shape;

d) said middle section including a cut-out section defining a wedge-shape for use in the collection of at least one sample of the blend matrix; said wedge-shape section further including at least one interior insert chamber for receiving in each a sample collection cup for collecting a sample of the blend matrix;

e) said rear section including a cut-out section having a tapered cone section defining a tapered wedge-shape for preventing said sampling device from moving relative to the Z axis as said sampling device is inserted within the blend matrix;

f) said insert rod member for rotating said at least one sample collection cup relative to said at least one interior insert chamber;

g) said sampler extension member connected to said sample collection member and including a substantially tubular housing for receiving said insert rod member; and h) said insert rod member including a handle member for rotating said insert rod member.

2. A sampling device in accordance with claim 1, wherein said front, said middle and said rear sections, respectively, of said sample collection member include first, second and third inner pairs of wall surfaces thereon.

3. A sampling device in accordance with claim 2, wherein one of said second inner walls includes at least one plate cover having a U-shaped cut-out opening for covering of at least one of said interior insert chambers in order for at least one of said sample collection cups to pass through said U-shaped cut-out opening.

4. A sampling device in accordance with claim 2, wherein said second inner pair of wall surfaces of said cut-out section defining a wedge-shape of said middle section of said sample collection member form a wedge-shaped opening having an angle α in the range of 110° to 140°.

5. A sampling device in accordance with claim 2, wherein said third inner pair of wall surfaces of said cut-out section having a tapered cone section defining a wedge-shape of said rear section of said sample collection member form a wedge-shaped opening having an angle a in the range of 110° to 140°.

6. A sampling device in accordance with claim 2, wherein said first inner pair of wall surfaces of said tapered cone tip having said cut-out section defining said tapered wedge-shape of said front section of said sample collection member form a wedge-shaped opening having an angle α in the range of 110° to 140°.

7. A sampling device in accordance with claim 2, wherein said second inner pair of wall surfaces of said cut-out section defining a wedge-shape of said middle section of said sample collection member form a wedge-shaped opening having an angle α of 120°.

8. A sampling device in accordance with claim 2, wherein said third inner pair of wall surfaces of said cut-out section having a tapered cone section defining a wedqe-shape of said rear section of said sample collection member form a wedge-shaped opening having an angle α of 120°.

9. A sampling device in accordance with claim 2, wherein said first inner pair of wall surfaces of said tapered cone tip having said cut-out section defining said tapered wedge-shape of said front section of said sample collection member form a wedge-shape opening having an angle α of 120°.

10. A sampling device in accordance with claim 1, wherein said rear section of said tubular housing of said sample collection member includes a first connection means for attaching to said sampler extension member.

11. A sampling device in accordance with claim 10, wherein said first connection means includes a male connection member having spiral threading thereon.

12. A sampling device in accordance with claim 1, wherein said tubular housing of said sampler extension member includes at one end a second connection means for attaching to said sample collection member; and at the other end a rod insert component head having a hole opening therethrough for receiving of said insert rod member.

13. A sampling device in accordance with claim 12, wherein said rod insert component head includes a protective cap member having a reinforced top wall and a cylindrical side wall for protecting said rod insert component head from damage when the user is hammering said top wall of said protective cap member when manually inserting said sampling device into the powder blend matrix material.

14. A sampling device in accordance with claim 12, wherein said second connection means includes a female connection member having spiral threading therein.

15. A sampling device in accordance with claim 1, wherein said sample collection member is made of metals such as stainless steel, steel, or aluminum; or made from moldable and durable plastics for ease of cleaning and maintenance.

16. A sampling device in accordance with claim 1, wherein said sample extension member is made of metals such as stainless steel, steel, or aluminum; or made from moldable and durable plastics for ease of cleaning and maintenance.

17. A sampling device in accordance with claim 1, wherein said sample collection member has a length measurement between 12 and 21 inches, and diameter measurement between 1 and 6 inches.

18. A sampling device in accordance with claim 1, wherein said sample extension member has a length measurement between 12 and 60 inches, and a diameter measurement between 1 and 6 inches.

19. A sampling device in accordance with claim 1, wherein said insert rod member includes a rod component having a semi-cylindrical rod shape; said rod component has a length measurement between 10 and 58 inches, and a diameter measurement between ¼ inch to ½ inch.

20. A sampling device in accordance with claim 1, wherein each of said sample collection cups includes an outer semi-cylindrical wall and a pair of side walls for forming an interior compartment and having an outer perimeter edge for receiving therein a precise amount of the dry powder blend matrix material.

21. A sampling device in accordance with claim 20, wherein each of said side walls of said sample collection cups includes a semi-circular hole opening having a semi-circular cylindrical holding member therethrough for receiving therein said insert rod member in which to rotate said sample collection cup in a circular direction.

22. A sampling device in accordance with claim 1, wherein said sampling device for taking powder samples from different sized containers selected from a group consisting of blenders, silos, mixers, tote bins, pails, drums, fiber containers, and vats.

23. A rotatable sampling device for obtaining at least one sample of a dry powder blended material from the powder blend matrix within a container, comprising:
  a) a sampling device including a sample collection member and an insert rod member;
  b) said sample collection member including a substantially tubular housing having at least one cut-out section defining a wedge-shape for inserting into the blend matrix to be sampled;
  c) said sample collection member including at least one interior insert chamber for receiving a sample collection cup for collecting a sample of the blend matrix; and
  d) said insert rod member for rotating said at least one sample collection cup relative to said at least one interior insert chamber.

24. An automated rotatable sampling device for obtaining at least one sample of a dry powder blended material from the powder blend matrix within a container, comprising:
  a) a sampling device;
  b) an adjustable frame assembly having movable and adjustable front, rear, and side bars having attachment means thereon for mounting on different size containers;
  c) an carriage assembly mounted on said adjustable frame assembly and having moving means for moving said sampling device in the X, Y, and Z directions relative to said container;
  d) said sampling device including a sample collection member having a substantially tubular housing including a front section, a middle section and a rear section;
  e) said front section including a tapered cone tip having a cut-out section defining a tapered wedge-shape for inserting into the blend to be sampled;
  f) said middle section including a cut-out section defining a wedge-shape for use in the collection of at least one sample of the blend matrix; said wedge-shape section further including at least one interior insert chamber for receiving in each a sample collection cup for collecting a sample of the blend matrix;
  g) said rear section including a cut-out section having a tapered cone section defining a tapered wedge-shape for preventing said sampler device from moving relative to said Z direction as said sampling device is inserted within the blend matrix;
  h) said sample collection member including an insert rod member for rotating said at least one sample collection cup within said at least one interior insert chamber;
  i) a sampler extension member connected to said sample collection member and including a substantially tubular housing for receiving therein said insert rod member; and
  j) said insert rod member including a handle member for rotating said insert rod member.

25. An automated sampling device in accordance with claim 24, wherein said attachment means are selected from a group consisting of clamps, fasteners, bolts, and suction clamps.

26. An automated sampling device in accordance with claim 24, wherein said moving means includes a first motor for moving said sampling device in said X direction; a second motor for moving said sampling device in said Y direction; and a third motor for moving said sampling device in said Z direction.

27. An automated sampling device in accordance with claim 26, wherein said frame assembly is connected to a fourth motor for rotating said insert rod member in a clockwise or counter-clockwise movement.

28. An automated sampling device in accordance with claim 27, wherein said carriage assembly is electronically connected to a control panel and a power source.

29. An automated sampling device in accordance with claim 28, wherein said control panel includes a plurality of control members and a visual display screen having a keyboard for programming the output functions of positioning said sampling device along specific points on said X, Y and Z axis directions; for selecting an angle β in moving and angling said sampling device along the Z axis direction via a ratchet plate member; for rotating said insert rod member; and for powering up said first, second, third and fourth electric motors, respectively, via said power source.

30. An automated sampling device in accordance with claim 24, wherein said carriage assembly further includes a collar member for attaching to said second and third motors.

31. An automated sampling device in accordance with claim 24, wherein said carriage assembly further includes a rachet plate member having a ball bearing component for enabling said sampling device to be angled up to a 60° degree angle from the Z axis direction.

32. An automated sampling device in accordance with claim 24, wherein said adjustable frame assembly is made from light-weight metals, or from durable and rigid plastics.

33. An automated sampling device in accordance with claim 24, wherein said carriage assembly is made from light-weight metals, or from durable and rigid plastics.

34. An automated sampling device in accordance with claim 24, wherein said sampling device for taking powder samples from different sized containers that are selected from a group consisting of blenders, silos, mixers, tote bins, pails, drums, fiber containers, and vats.

35. An automated sampling device in accordance with claim 24, wherein said front, said middle and said rear sections, respectively, of said sample collection member include first, second and third inner pairs of wall surfaces thereon.

36. An automated sampling device in accordance with claim 35, wherein one of said second inner walls includes at least one plate cover having a U-shaped cut-out opening for covering of at least one of said interior insert chambers in order for at least one of said sample collection cups to pass through said U-shaped cut-out opening.

37. A sampling device in accordance with claim 35, wherein said second inner pair of wall surfaces of said cut-out section defining a wedge-shape of said middle section of said simple collection member form a wedge-shaped opening having an angle $\alpha$ in the range of 110° to 140°.

38. A sampling device in accordance with claim 35, wherein said third inner pair of wall surfaces of said cut-out section having a tapered cone section defining a wedge-shape of said rear section of said sample collection member form a wedge-shaped opening having an angle $\alpha$ of 120°.

39. An automated sampling device in accordance with claim 35, wherein said first inner pair of wall surfaces of said tapered cone tip having said cut-out section defining said tapered wedge-shape of said front section of said sample collection member form a wedge-shaped opening having an angle $\alpha$ in the range of 110° to 140°.

40. A sampling device in accordance with claim 32, wherein said first inner pair of wall surfaces of said tapered cone tip having said cut-out section defining said tapered wedge-shape of said front section of said sample collection member form a wedge-shape opening having an angle $\alpha$ of 120°.

41. A sampling device in accordance with claim 35, wherein said third inner pair of wall surfaces of said cut-out section having a tapered cone section defining a wedge-shape of said rear section of said sample collection member form a wedge-shaped opening having an angle $\alpha$ in the range of 110° to 140°.

42. A sampling device in accordance with claim 35, wherein said second inner pair of wall surfaces of said cut-out section defining a wedge-shape of said middle section of said sample collection member form a wedge-shaped opening having an angle $\alpha$ of 120°.

43. An automated sampling device in accordance with claim 24, wherein said rear section of said tubular housing of said sample collection member includes a first connection means for connectedly attaching to said sampler extension member.

44. An automated sampling device in accordance with claim 43, wherein said first connection means includes a male connection member having spiral threading thereon.

45. An automated sampling device in accordance with claim 4, wherein said rod insert component head includes a protective cap member having a reinforced top wall and a cylindrical side wall for protecting said rod insert component head from damage when the user is hammering said top wall of said protective cap member when manually inserting said sampling device into the powder blend matrix material.

46. An automated sampling device in accordance with claim 24, wherein said tubular housing of said sampler extension member includes at one end a second connection means for connectedly attaching to said sample collection member; and at the other end a rod insert component head having a hole opening therethrough for receiving said insert rod member.

47. An automated sampling device in accordance with claim 46, wherein said second connection means includes a female connection member having spiral threading therein.

48. An automated sampling device in accordance with claim 24, wherein said sample collection member is made of metals such as stainless steel, steel, or aluminum; or made from moldable and durable plastics for ease of cleaning and maintenance.

49. An automated sampling device in accordance with claim 24, wherein said sample extension member is made of metals such as stainless steel, steel, or aluminum; or made from moldable and durable plastics for ease of cleaning and maintenance.

50. An automated sampling device in accordance with claim 24, wherein said sample collection member has a length measurement between 12 and 21 inches, and a diameter measurement between 1 and 6 inches.

51. An automated sampling device in accordance with claim 24, wherein said sample extension member has a length measurement between 12 and 60 inches, and a diameter measurement between 1 and 6 inches.

52. An automated sampling device in accordance with claim 24, wherein said insert rod member includes a rod component having a semi-cylindrical rod shape; said rod component has a length measurement between 10 and 58 inches, and a diameter measurement between ¼ inch to ½ inch.

53. An automated sampling device in accordance with claim 24, wherein each of said sample collection cup includes an outer semi-cylindrical wall and a pair of side walls for forming an interior compartment and having an outer perimeter edge for receiving therein a precise amount of the dry powder blend matrix material.

54. An automated sampling device in accordance with claim 53, wherein each of said side walls of said sample collection cups includes a semi-circular hole opening having a semi-circular cylindrical holding member therethrough for receiving therein said insert rod member in which to rotate said sample collection cup in a circular direction.

* * * * *